US009351660B2

(12) United States Patent
Gilmore et al.

(10) Patent No.: US 9,351,660 B2
(45) Date of Patent: May 31, 2016

(54) BIOMEDICAL ELECTRODE CONFIGURATION FOR SUPPRESSING MOVEMENT ARTIFACT

(75) Inventors: L. Donald Gilmore, Wellesley, MA (US); Gianluca De Luca, Natick, MA (US); Carlo J. De Luca, Wellesley, MA (US)

(73) Assignee: Altec, Inc., Natick, MA (US)

( * ) Notice: Subject to any disclaimer, the term of this patent is extended or adjusted under 35 U.S.C. 154(b) by 16 days.

(21) Appl. No.: 13/437,263

(22) Filed: Apr. 2, 2012

(65) Prior Publication Data

US 2012/0190960 A1   Jul. 26, 2012

Related U.S. Application Data

(62) Division of application No. 12/583,656, filed on Aug. 24, 2009.

(60) Provisional application No. 61/271,930, filed on Jul. 28, 2009.

(51) Int. Cl.
*A61B 5/04* (2006.01)
*A61B 5/0488* (2006.01)
*A61B 5/0492* (2006.01)
*A61B 5/00* (2006.01)

(52) U.S. Cl.
CPC ............. *A61B 5/0488* (2013.01); *A61B 5/0492* (2013.01); *A61B 5/7214* (2013.01)

(58) Field of Classification Search
CPC .. A61B 5/0402; A61B 5/0408; A61B 5/0424; A61B 5/0428; A61B 5/721
USPC .................. 600/372, 382, 384, 386, 393, 395
See application file for complete search history.

(56) References Cited

U.S. PATENT DOCUMENTS

| | | | | |
|---|---|---|---|---|
| 4,619,266 A * | 10/1986 | Hodgson | ........................ | 600/393 |
| 6,032,064 A * | 2/2000 | Devlin et al. | ................. | 600/383 |
| 6,480,731 B1 * | 11/2002 | DeLuca et al. | ................ | 600/393 |
| 6,912,414 B2 * | 6/2005 | Tong | ............................. | 600/372 |
| 2002/0147411 A1 * | 10/2002 | Lutz | ................... | A61B 5/04004 600/544 |
| 2003/0083559 A1 * | 5/2003 | Thompson | .................... | 600/372 |
| 2003/0187490 A1 * | 10/2003 | Gliner | .................. | A61N 1/0531 607/116 |
| 2005/0113703 A1 * | 5/2005 | Farringdon et al. | ........... | 600/509 |
| 2006/0079801 A1 * | 4/2006 | DeLuca et al. | ................ | 600/546 |
| 2007/0142735 A1 * | 6/2007 | Shin et al. | ..................... | 600/509 |
| 2008/0045775 A1 * | 2/2008 | Lozano | .............. | A61N 1/36014 600/12 |

* cited by examiner

*Primary Examiner* — Joseph Stoklosa
*Assistant Examiner* — Brian M Antiskay
(74) *Attorney, Agent, or Firm* — Muirhead and Saturnelli, LLC

(57) ABSTRACT

A biomedical sensor for detecting EMG signals may include a non-conducting fixed framework supporting a symmetrical arrangement of four electrode surfaces, configured as two signal detection contacts, each with a respective associated signal reference contact. The mechanical and electrical configuration act together to suppress movement artifact.

13 Claims, 8 Drawing Sheets

BIOMEDICAL ELECTRODE CONFIGURATION FOR SUPPRESSING MOVEMENT ARTIFACT

RELATED APPLICATIONS

This application is a divisional of U.S. application Ser. No. 12/583,656 filed on Aug. 24, 2009 (pending) which claims priority to U.S. Provisional Application No. 61/271,930 filed on Jul. 28, 2009, which is hereby incorporated by reference.

TECHNICAL FIELD

This application relates to the field of sensing bio-potentials generated within a living body and, more particularly, to sensors placed on the surface of the skin for detecting the electrical activity from muscles.

BACKGROUND OF THE INVENTION

Depolarization potentials created during a muscle fiber contraction generate an electrical field gradient which propagates in a direction along the fibers throughout the volume conductor comprised of the muscle, the surrounding tissue, and skin layers. Electrodes placed on the skins surface allow for the non-invasive detection of this electrical field gradient providing the temporal summation of the propagating depolarization potentials of the active muscle fibers in the underlying vicinity of the electrode. The resulting voltage on the skin's surface is termed the surface electromyographic signal (sEMG).

In order to measure this voltage, an electrolytic interface may be formed between the electrolytes in the subcutaneous tissue and the ohmic conductive surface of the electrode contact attached to the skins surface. The primary electrical conduit between the subcutaneous volume conductor and the skins surface is established via the sweat ducts which pass through the non-conductive stratum corneum so that sweat and moisture from the underlying sweat glands are deposited onto the skins surface completing the electrolytic interface.

The electrolytic interface is provided by disassociated ions from the electrolyte forming a layer on the conductive electrode contact surface (Nernst polarization or contact half-cell potential). Depending on the chemical composition, concentration of the electrolytes on the skin, and the composition of the electrode contact metal, the half-cell potentials can range in amplitude to several hundred millivolts. Signal potentials emanating from the muscle in the underlying tissue are conveyed via ionic transport through the electrolyte to the exposed conductive contact surface of the electrode. The signal amplitude is typically several orders of magnitude smaller than the half-cell potential and ranges from 10 microvolts to 5 millivolts. The resultant voltage sensed by the electrode contact is therefore the electrical summation of the signal potential and contact half-cell potential.

When the electrolytic skin interface of the electrode is mechanically disturbed due to relative movement or pressure changes between the tissue and conductive surface of the electrode, the effective concentration of the electrolytes can be altered so that the resultant half-cell potential amplitude is modulated by the mechanical disturbance. The modulation of hall-cell potential is termed "movement artifact" and typically arises from rapid body movements, or objects or clothing coming into contact with the sensor case housing the electrodes.

Movement artifact can be particularly problematic as the change in half-cell potential can exhibit large (>50 mV) voltage deviations which overwhelm the amplitude of the sEMG signal. An additional source of movement artifact is due to the triboelectric charge that can accumulate on the non-conducting stratum corneum as a result of walking on carpet or contact with certain fabrics under low humidity conditions. This effect can be especially problematic when the electrolytic skin interface exhibits high impedance resulting from the lack of suitable moisture between the electrode contact and the skin. This impedance can reach tens of megohms for contacts with an area of 1 mm squared placed on unprepared skin.

Prior art techniques developed to address reduction in movement artifact focus on the materials used to fabricate the conductive surface of the electrode contact. Highly conductive aqueous salt solutions or hydrophilic gels applied to the contacts surface act to improve the electrolytic skin interface by augmenting the nature moisture present on the skins surface to stabilize and reduce skin impedance, however these materials can create large half-cell potentials, and if not properly applied, can leak to form low impedance bridges between electrode contacts thereby "shorting out" the desired biopotential signal. Electrodes formed as an insulating capacitive plate overcome some of the problems associated with half-cell potential created when using ohmic electrodes, but are subject to the triboelectric charge effect on dry stratum corneum, and therefore subject to movement artifact and static discharge when placed under clothing. The class of "dry" electrodes formed from silver metal or silver coated plastic contacts falls in between the two extremes of gel and capacitive electrode designs. They have higher initial impedance than gel, relying on the inherent moisture present on the skin to form the electrolytic interface. They are typically formed of pure silver or silver-silver chloride.

Regardless of the contact materials used, it is known that the configuration of a sensor designed to detect sEMG signals may include two disposable electrode contact discs, one for each signal input placed singularly, or in pairs, mounted on a flexible non-conductive adhesive pad so that the applied contact conforms to the underlying body surface. The electrodes may be attached by snaps or spring loaded clips and connected to remote electronic circuitry via a shielded insulated tethered cable.

Characteristically, the sensor includes the two signal contacts located over the muscle and a third "reference" contact located at an electrically inactive location on the body. In some sensors the two signal and reference contacts are placed on the same insulating pad in the form of an equilateral triangle. The orientation for the signal input contact pair may be in a direction parallel to the muscle fiber. The recording configuration may be the differential configuration where the voltage at each signal input contact is measured with respect the third reference contact and subtracted using a differential pre-amplifier circuit. In this way, any voltages common to both electrodes such as half-cell potentials and line interference effectively subtract to zero for an ideal amplifier. However, in compliant or flexible electrode skin interface designs, disturbances to the electrode interface induced from contact forces applied directly to the interface or induced from shear forces applied to the skin are likely to cause an unequal localized disruption of the electrolyte junction half-cell potential of each electrode contact. This unequal change in half-cell potentials can not be removed by differential subtraction and as a result generates a movement artifact signal.

As further background to the system described herein, sEMG sensors with or without onboard signal conditioning circuitry are typically tethered via a cable which acts to power and convey the output signal from the sensor to external instrumentation. With the advent of wireless technology, wireless versions of sEMG sensors are becoming an alternative to tethered sensors. These sensors typically dispense with the reference ground contact due to the fact that unlike tethered designs, they electrically "float" with respect to earth ground. These are termed "reference free" designs. The two electrode sensor can be configured either as a mono-polar, or as a differential amplifier with an internally generated electrical reference. Both configurations measure the voltage difference measured between the two contacts. A typical wireless sensor consists of two gel filled disk contacts mounted on disposable adhesive backed pad. Snap leads connect the electrodes via a short cable to the inputs of a wireless module containing the sEMG signal conditioning electronics.

All of the aforementioned electrode contact and sensor configurations described as prior art, whether tethered or wireless, are subject to the effects of movement induced artifact, due to inability to electrically stabilize the electrolytic interface during a mechanical disturbance to the electrode contacts. The commonly-applied technique to mitigate sensitivity to movement artifact is to decrease and stabilize the impedance of the skin-electrode interface using conductive aqueous salt solutions or hydrophilic gels applied to disposable electrodes. When combined with a differential recording configuration using a remote reference, these solutions are partially effective but incur the problems associated with application of pastes or dehydration of gels over time, limiting their useful self-life.

The problems of artifact and sensitivity to electro-static fields are especially severe for wireless "reference free" sEMG sensor designs which use only two contacts. Wireless solutions utilizing differential recording from a triangular configuration of three disposable electrodes, while less affected by electro-static fields, are still subject to movement induced artifacts.

Accordingly, it would be desirable to provide an electrode configuration which when applied to unprepared skin, can suitably detect muscle signals during highly dynamic activities, while suppressing associated movement artifact. Furthermore, the electrode configuration would be directly applicable to wireless sEMG sensor technologies which provide the inherent benefit of un-tethered, unencumbered measurement from muscles during these types of activities.

SUMMARY OF THE INVENTION

According to the system described herein, a biomedical sensor includes a substrate and a plurality of conductive areas arranged on the substrate and configured as signal detection contacts each with a respective associated signal reference contact, forming a plurality of signal detection/reference contact pairs. A differential sensing circuit is included, in which each signal detection/reference contact pair reacts in response to an electrical artifact manifestation of an applied mechanical disturbance, and wherein at least one common electrical component of the artifact measured by the plurality of signal detection/reference contact pairs is cancelled out by the differential sensing circuit. The substrate may be rigid.

A fixed framework may be coupled to the substrate, in which the substrate is a body-directed electrically insulating bottom surface of the framework, forming an electrode to body interface. A symmetrical arrangement of two signal input and two signal reference contacts may be retained by the fixed framework, each having a contact surface projecting from the bottom surface and a coupling surface projecting above the top surface. The system described herein relates to a type of electrode configuration which can suppress movement induced electrical artifacts. The system described herein is based on the concept that unlike existing compliant designs typical of disposable electrodes, a fixed, non-compliant framework supporting a symmetrical arrangement of conductive areas provides for the mechanical stabilization of the underlying tissue.

The four conductive areas, when configured as two signal detection contacts, each with a respective associated signal reference contact in nearby proximity, may react similarly and in unison to the electrical artifact manifestation of an applied mechanical disturbance in such a way that the resulting common electrical components of the artifact can be canceled out by a differential sensing circuit configuration. The four conductive areas may be disposed and formed according to various embodiments of the system described herein. The symmetrical arrangement of the contacts may be configured as two signal detection contacts, each with a respective associated signal reference contact in nearby proximity, forming two signal/reference contact pairs. The signal/reference contact pairs may form two co-linear detection/reference contact pairs oriented in parallel with respect to each other and spaced apart so that the detection contact is aligned to be on the same side of each pair.

Furthermore, each of the four conductive areas may be formed in the shape of a conductive rod aligned in parallel on the plane of the body-directed insulating substrate, and projecting from the body-directed fixed substrate. The body-directed insulating bottom surface substrate may be contoured to surround each of the four projecting conductive areas. Each of the four conductive areas may be formed in the shape of a disc attached to and coplanar with the body-directed insulating bottom surface substrate and/or may be formed in the shape of a dome whose cross-sectional profile exhibits a curved concave shape attached to and projecting from the body-directed insulating bottom surface substrate. Each of the four conductive contact areas may be formed of substantially identical material composition, size and shape. Each of the four conductive areas may be formed from a noble metal and/or may be formed from a conductive plastic and/or each of the four conductive areas may be formed from a conductive region matrix integrated within the matrix of the insulating substrate.

The insulating bottom surface substrate may be composed of non-conductive, non-polarizable, low triboelectric, biocompatible materials. The insulating bottom surface substrate may be attached to the skin by means of a double-sided adhesive membrane sheet with cut-out areas aligned with the perimeter of each of the four conductive areas.

The fixed framework may include a protective enclosure with multi-conductor cable having individual insulated conductors interconnected with the coupling surface of the contacts so that only the conductive areas are exposed. The protective enclosure may retain a wireless transceiver, and power supply, and differential amplifier interconnected with the coupling surface of the contacts so that only the conductive areas are exposed. The enclosure may include an indicating marker aligned in parallel with the preferred orientation and of the sensor with respect to the direction of signal propagation and delineating the location of the signal input contacts.

BRIEF DESCRIPTION OF THE DRAWINGS

Embodiments of the system described herein will be explained in detail below according to the figures, which are briefly described as follows.

DETAILED DESCRIPTION OF VARIOUS EMBODIMENTS

Figure 1:
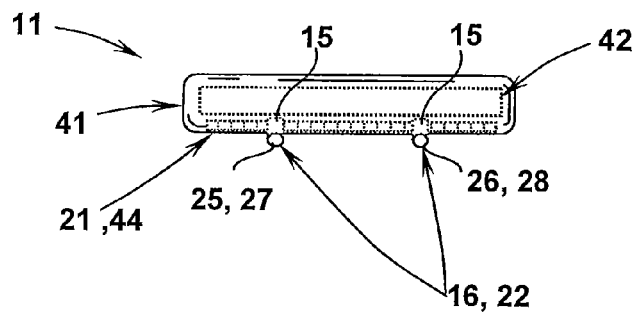
FIG. 1 is an elevation view of a biomedical sensor according to an embodiment of the system described herein.
Figure 2:
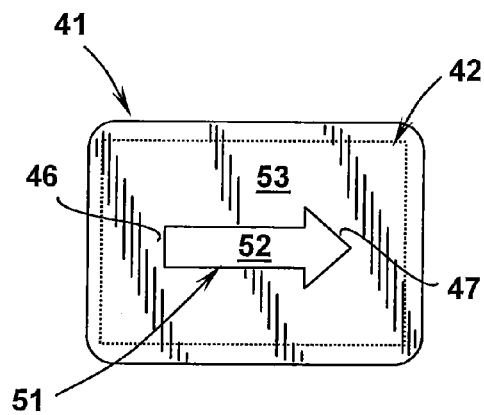
FIG. 2 is a top view of the case component of the sensor shown in FIG. 1.
Figure 3:
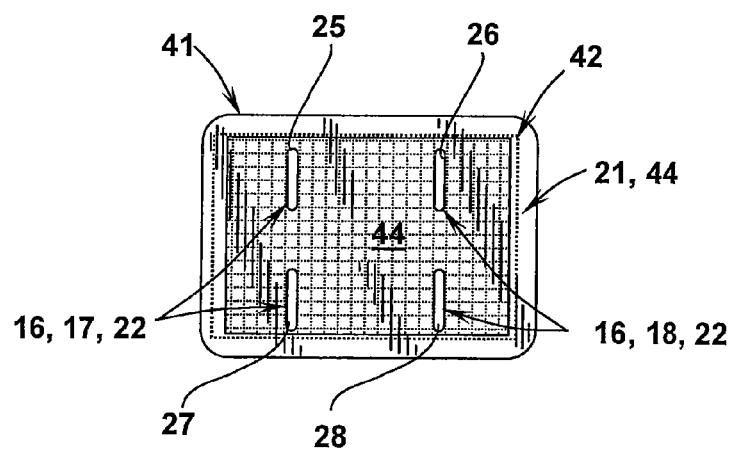
FIG. 3 is a bottom view of fixed framework substrate retaining contacts shown in FIG. 1.

A biomedical sensor 11 includes a molded case 41 that retains a preamplifier and associated electronics 42 for wireless transmission of the detected signal as illustrated in FIG. 1. Disposed on the bottom surface 21 of the case 41, or other type of framework, may be a rigid fixed substrate surface 44. Disposed on the substrate surface 44 of the case 41 (FIG. 3) may be a symmetrical, parallel array of cylindrical bar contacts 16 each retained by a projecting portion 15 electrically interconnected with the preamplifier 42. Included among the contacts 16 are two pairs of contacts 17, 18. One pair of contacts 17 may include a positive signal detection contact 25 and a reference contact 27. A second pair of contacts 18 may include a negative signal detection contact 26 and a reference contact 28. The two signal detection contacts 25, 26 and the two reference contacts 27, 28 may be linearly aligned with respect to the case indicia 51 disposed on the top surface 53 of the case 41 illustrated in FIG. 2, and arranged so that that one contact pair 17 is positioned with respect to the tail 46 of the arrow 52 and one contact pair 18 is positioned with respect to the head 47 of the arrow 52. The contact pairs 17, 18 may be further arranged so that the signal detection contacts 25, 26 are linearly aligned with respect to each other and oriented in parallel to the axis of the arrow 52. Similarly, the reference contacts 27, 28 may be linearly aligned with respect to each other and oriented in parallel to the axis of the arrow 52. Each of the cylindrical contacts 16 may be formed from a suitable electrically conductive material with an exposed contact surface 22 of equal area.

Figure 4:
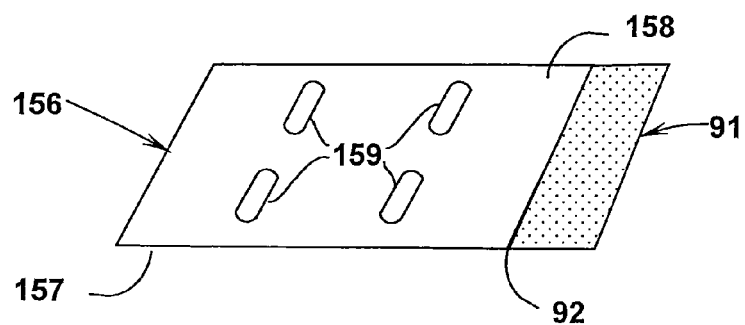
FIG. 4 is a perspective view of the double sided adhesive interface used with the sensor of FIG. 1.

Also included in the sensor embodiment 11 may be an attachment interface 156 shown in FIG. 4 having an adhesive interface surface 157 for securing the interface 156 to the case 41 and an adhesive interface surface 158 for securing the case 41 to the skin 61 of the subject. The interface 156 defines a plurality of apertures 159 in the form of slots disposed to receive the contacts 16. Tab 91 may be attached to one end 92 of the top surface 157 of the interface 156.

Figure 5:
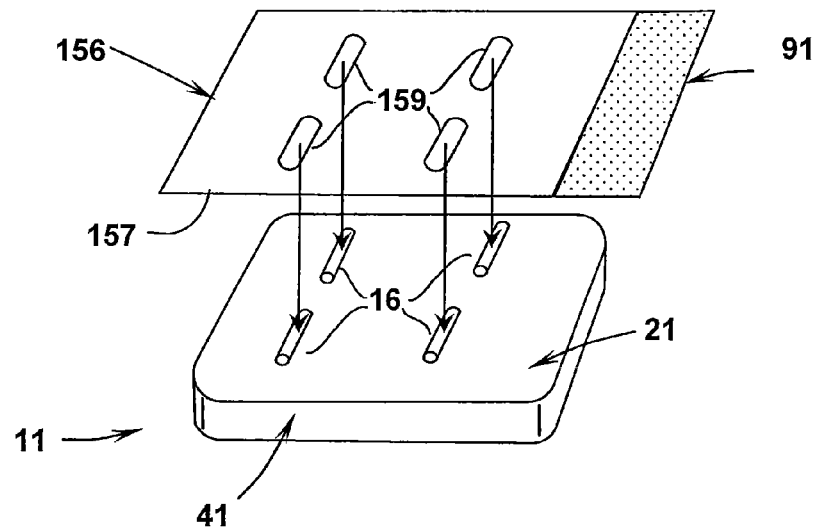
FIG. 5 is a perspective view of the double sided adhesive interface positioned for attachment to the sensor of FIG. 1.
Figure 6:
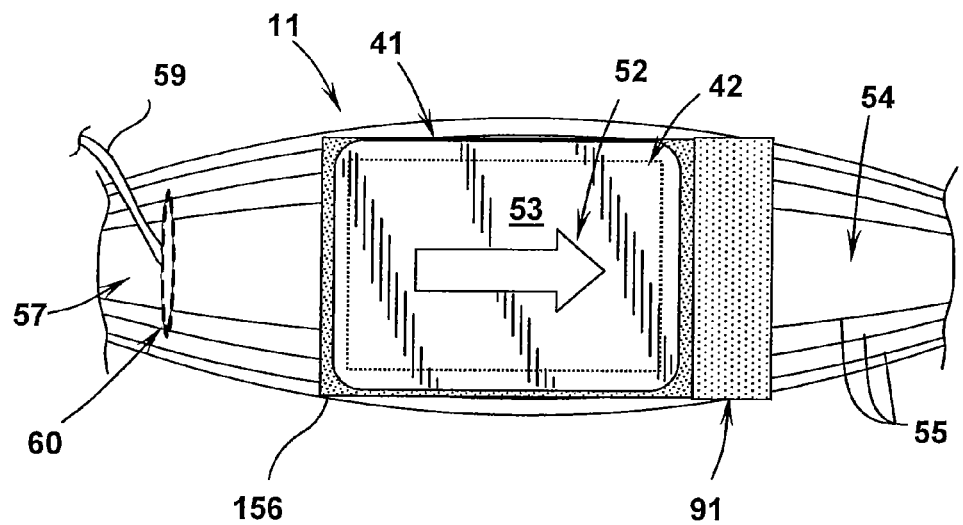
FIG. 6 is a schematic top view of the sensor of FIG. 1 mounted adjacent to a bundle of muscle fibers.
Figure 7:
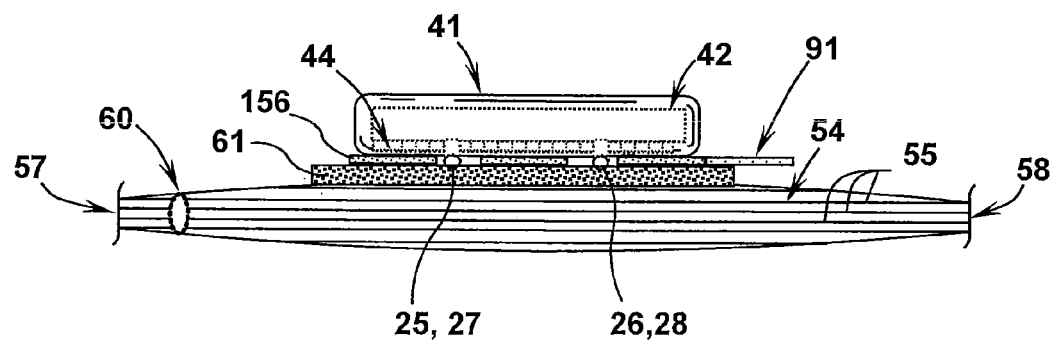
FIG. 7 is a schematic side view of the sensor and muscle fiber bundle shown in FIG. 6.

Prior to use of the sensor 11, the top adhesive surface 157 of the attachment interface 156 may be positioned (FIG. 5) so that each apperture 159 is aligned and centered with its respective contact 16. and then attached to the bottom surface 21 of the case 41. Next, the adhesive bottom surface 158 of the attachment interface 156 may be adhered to the skin 61 of the subject using the arrow 52 to orient the sensor 11 with respect to the muscle fibers 55. Proper orientation aligns the arrow 52 with the fibers 55 of the bundle 54 and pointed in a direction from the proximal end 57 toward the distal end 58 of the bundle 54 as shown in FIGS. 6 and 7. The proximal end 57 may be located adjacent to an innervation zone 60 established at the terminal portion of the nerve 59. That arrangement of the sensor 11 may establish a known positive potential for the detector contact 25 and a negative potential for the detector contact 26.

Figure 8:
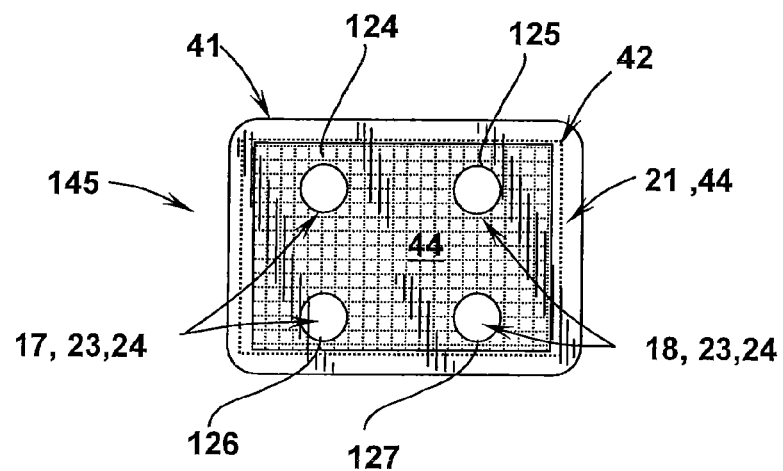
FIG. 8 is a plan view of another contact embodiment of the system described herein.
Figure 9:
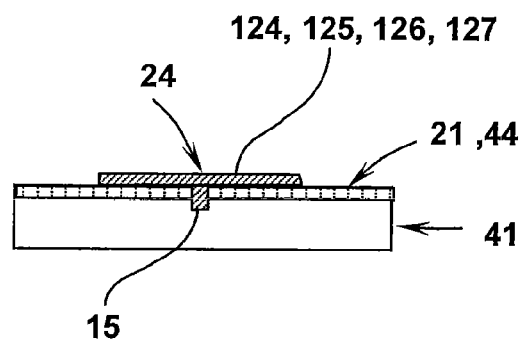
FIG. 9 is a partial cross-sectional view of the contact shown in FIG. 8.
Figure 10:
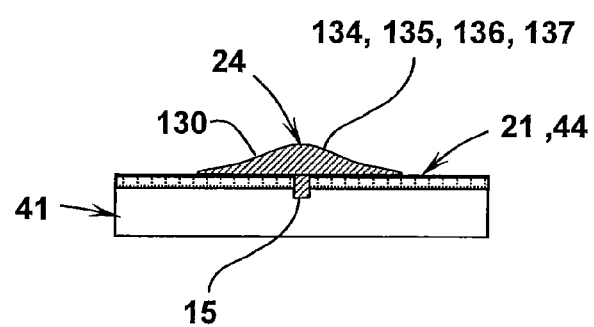
FIG. 10 is a partial cross-sectional view of an alternate form of the contact shown in FIG. 9.

Another biomedical sensor embodiment 145 is illustrated in FIGS. 8, 9, and 10. Disposed on the bottom surface 21 of the case 41 may be a rigid fixed substrate surface 44. Disposed on the substrate surface 44 of the case 41 (FIG. 3) may be a symmetrical, parallel array of disc contacts 23 each retained by a projecting portion 15 electrically interconnected with the preamplifier 42. Included among the contacts 23 are two pairs of flat disc contacts 17, 18. One pair of contacts 17 may include a positive signal detection contact 124 and a reference contact 126. A second pair of contacts 18 may include a negative signal detection contact 125 and a reference contact 127. The two signal detection contacts 124, 125 and the two reference contacts 126, 127 may be linearly aligned with respect to the case indicia 51 disposed on the top surface 53 of the case 41 illustrated in FIG. 2, and arranged so that that one contact pair 17 is positioned with respect to the tail 46 of the arrow 52 and one contact pair 18 is positioned with respect to the head 47 of the arrow 52.

The contact pairs 17, 18 may be further arranged so that the signal detection contacts 124, 125 are linearly aligned with respect to each other and oriented in parallel to the axis of the arrow 52. Similarly, the reference contacts 126, 127 may be linearly aligned with respect to each other and oriented in parallel to the axis of the arrow 52. Each of the disc contacts 23 may be formed from a suitable electrically conductive material with an exposed contact surface 24 of equal area. An alternative form of the disc contacts 23 is shown in FIG. 10. The contact surface 24 of each contact 134, 135, 136, 137 may be shaped in the form of dome with a curved concave cross-sectional profile 130. The profile 130 may form a catenary curve.

Figure 11:
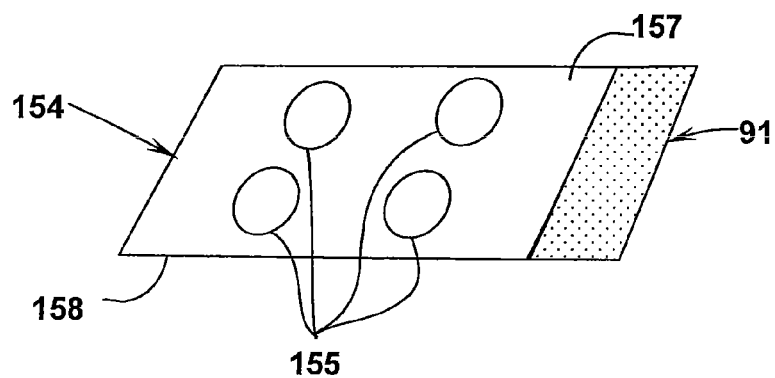
FIG. 11 is a perspective view of the double sided adhesive interface used with the electrodes of FIG. 8

Also included in the sensor embodiment 145 may be an attachment interface 154 shown in FIG. 11 having an adhesive interface surface 157 for securing the interface 156 to the case 41 and an adhesive interface surface 158 for securing the case 41 to the skin 61 of the subject. The interface 154 defines a plurality of apertures 155 in the form of circles disposed to receive the contacts 23. Tab 91 is attached to one end 92 of the top surface 157 of the interface 156. The sensor embodiment 145 may be used in a manner similar to that described above for the embodiment 11.

Figure 12:
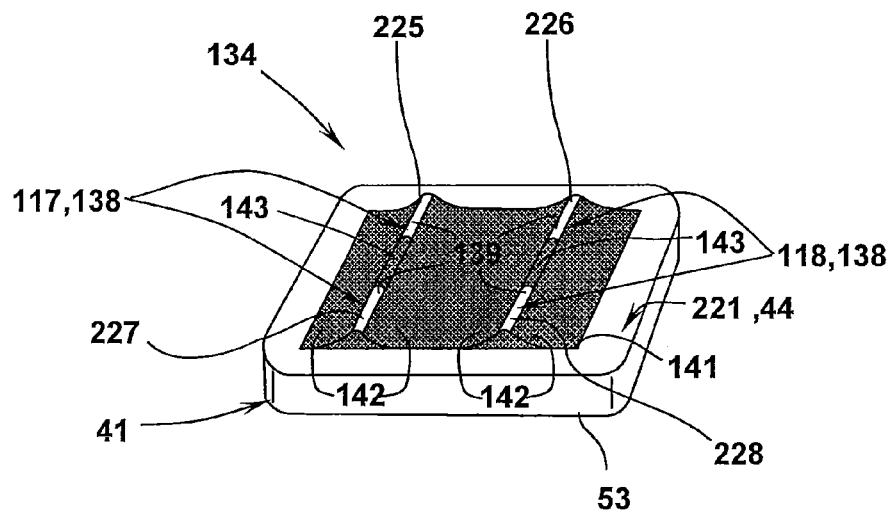
FIG. 12 is a perspective view of another biomedical sensor according to another embodiment of the system described herein.
Figure 13:
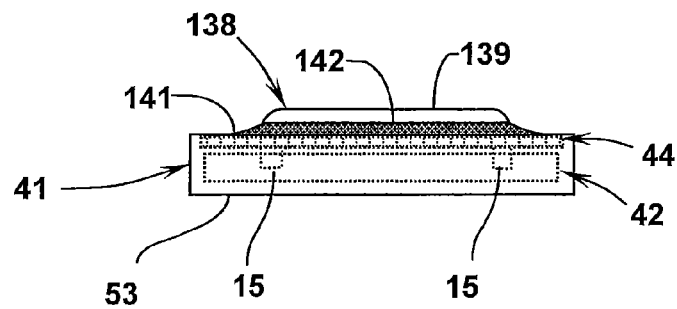
FIG. 13 is a side view of the contact used with the sensor of FIG. 12.

FIGS. 12 and 13 illustrate another biomedical sensor embodiment 134. An injection molded case 41 may retain a preamplifier and associated electronics 42 for wireless transmission of the detected signal as illustrated in FIG. 13. Disposed on the bottom surface 221 of the case 41 may be a rigid fixed substrate surface 44. Disposed on the substrate surface 44 of the case 41 (FIG. 12) may be a symmetrical, parallel array of elongated cylindrical bar contacts 138 retained by the rigid fixed substrate surface 44 and projecting outwardly from the bottom surface 53 of the case 41. An inwardly projecting portion 15 may electrically interconnect the contacts 138 with the preamplifier 42. Included among the contacts 138 may be two pairs of contacts 117, 118. One pair of contacts 117 may include a positive signal detection contact 225 and a reference contact 227. A second pair of contacts 118 may include a negative signal detection contact 226 and a reference contact 228. The two signal detection contacts 225, 226 and the two reference contacts 227, 228 may be linearly aligned with respect to the case indicia 51 disposed on the top surface 53 of the case 41 illustrated in FIG. 2, and arranged so that that one contact pair 117 is positioned with respect to the tail 46 of the arrow 52 and one contact pair 118 is positioned with respect to the head 47 of the arrow 52.

The contact pairs 117, 118 may be further arranged so that the signal detection contacts 225, 226 are linearly aligned with respect to each other and oriented in parallel to the axis of the arrow 52. Similarly, the reference contacts 227, 228 may be linearly aligned with respect to each other and oriented in parallel to the axis of the arrow 52. Each of the cylindrical contacts 138 may be formed from a suitable electrically conductive material with an exposed contact surface 222 of equal area. Each contact 138 may have an outer surface portion 139 for contacting the skin after attachment of the sensor 134. Included in the bottom surface 221 of the case may be a base portion 141 inwardly displaced from the outer surface contact portions 139 and concave transition portions 142 extending between the base portion 141 and the opposite edges of the outer surface portions 139 of each contact 138. Molded cylindrical regions 143 of the base portion 141 may be situated between the ends of each contact pair 117, 118 and act to form a continuation of the curve profile established by the transition portions 142. Each of the transition portions 142 may form a catenary curve to minimize the skin tensioning effect of the protruding contacts. In addition, the transition portions 142 may eliminate any cavities between the contacts 138 and the skin 61 which can accumulate sweat and thereby maintain a high impedance path in between the contacts 138.

Figure 14:
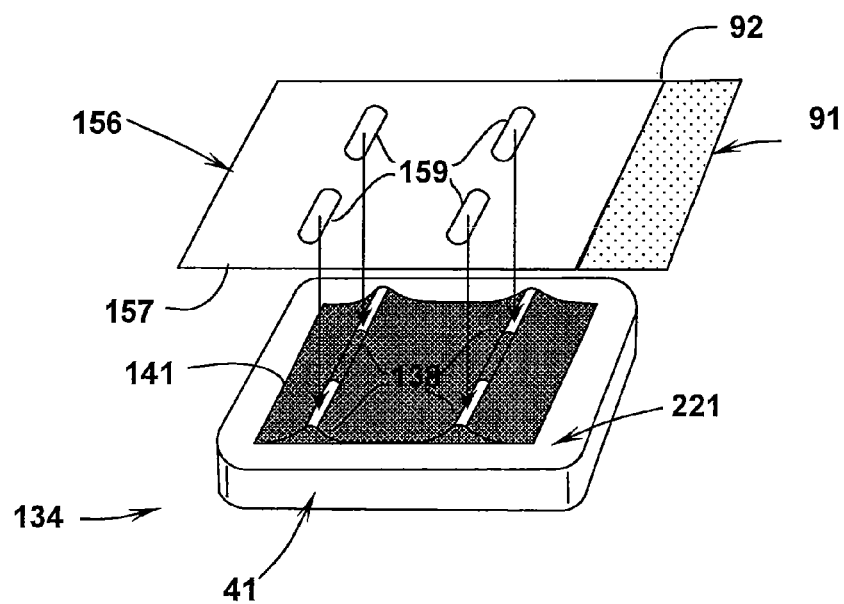
FIG. 14 is an assembly view of the sensor of FIG. 12 and adhesive interface shown in FIG. 4.

Also included in the sensor embodiment 134 may be an attachment interface 156 shown in FIG. 14 having an adhesive interface surface 157 for securing the interface 156 to the case 41 and an adhesive interface surface 158 for securing the case 41 to the skin 61 of the subject. The interface 156 defines a plurality of apertures 159 in the form of slots disposed to receive the contacts 138. Tab 91 is attached to one end 92 of the top surface 157 of the interface 156. The sensor embodiment 134 may be used in a manner similar to that described above for the embodiments 11 and 145.

Figure 15:
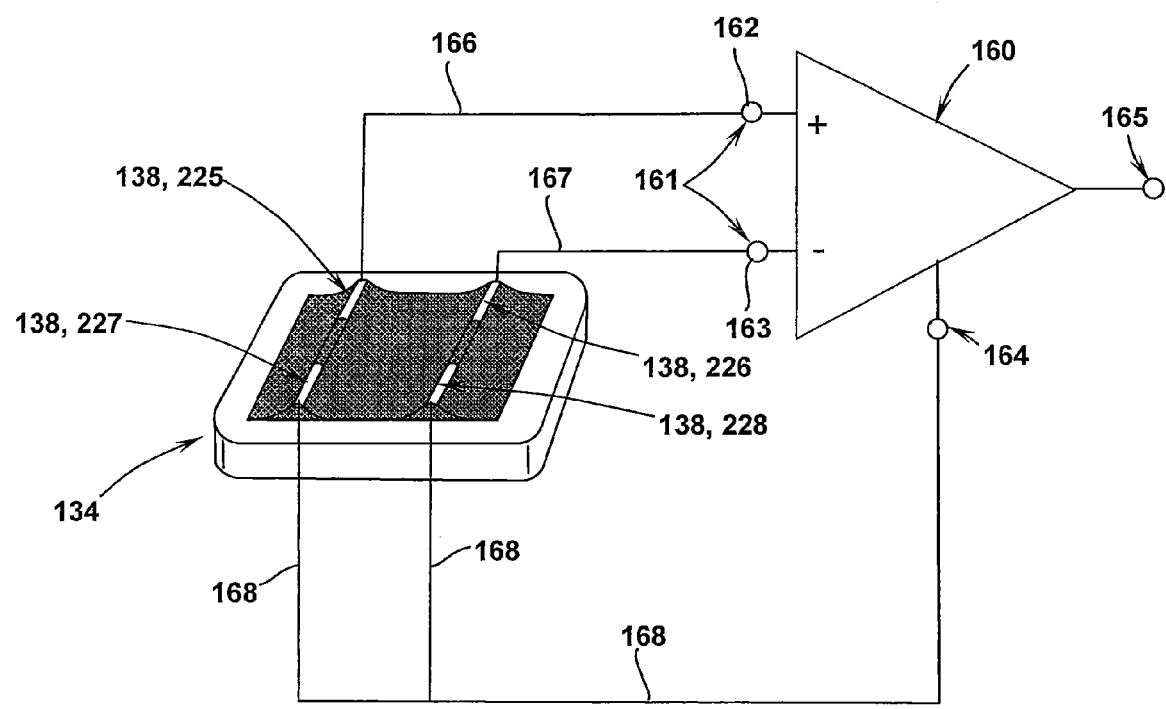
FIG. 15 is a schematic diagram of the differential amplifier recording configuration of the sensor of FIG. 12.

A schematic diagram of a differential preamplifier recording configuration that may be used with the biomedical sensor embodiments 11, 134, 145 is shown in FIG. 15. The sensor embodiment 134 shown previously in FIGS. 12 and 13 is used for illustrative purposes. A high impedance differential preamplifier 160 with differential inputs 161 may include a positive input 162 and a negative input 163, and a reference input 164 may be connected to the contacts 138 of biomedical sensor 134 using interconnections 166, 167, 168. The signal output 165 may be the arithmetic difference between the signal detected at contacts 225 and 226 measured with respect to the reference contacts 227, 228. The amplified output signal 165 may be interconnected with additional associated electronics 42 for wireless transmission of the detected signal.

Figure 16:
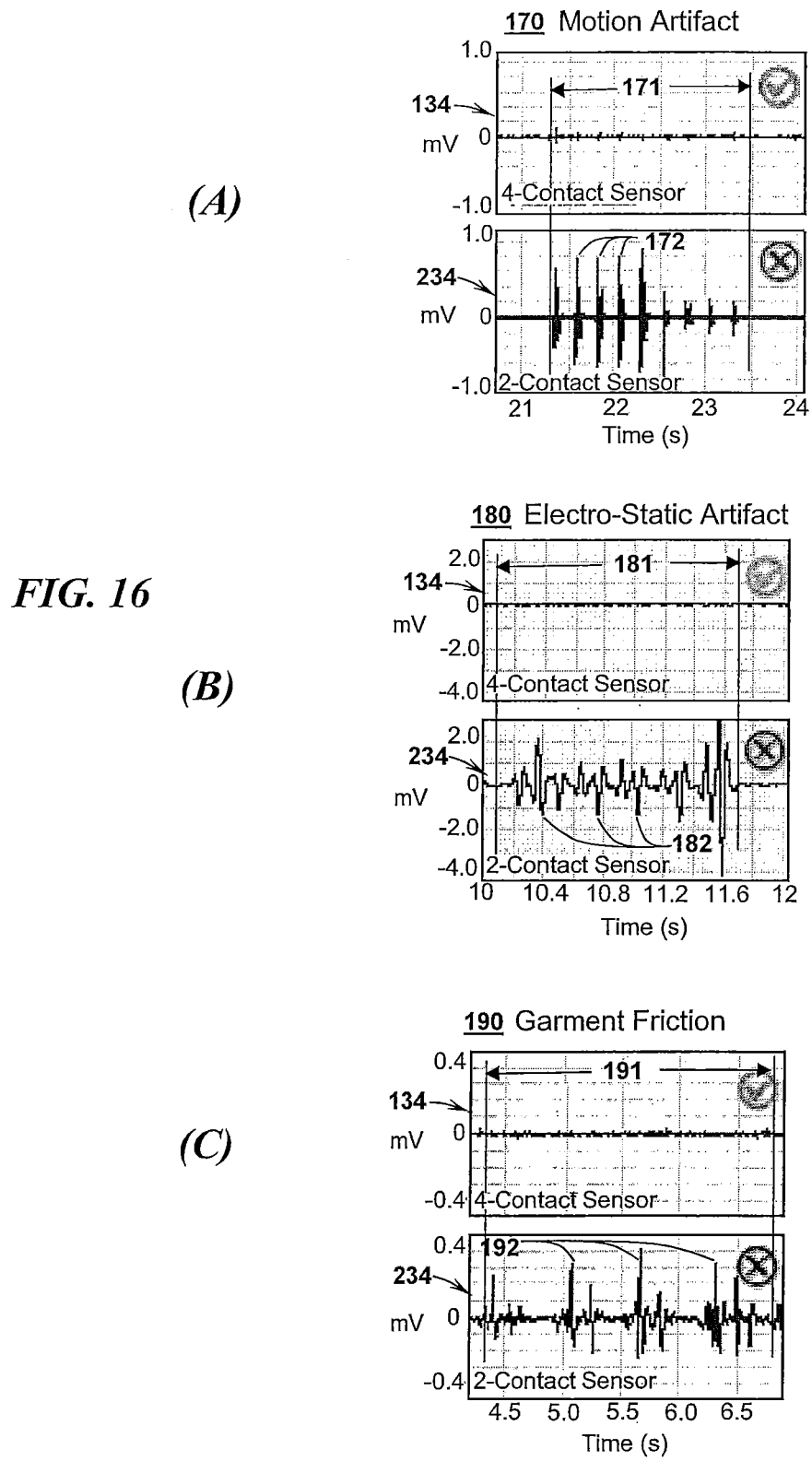
FIGS. 16A-C show a comparison of induced movement artifact of the sensor of FIG. 12 with respect to a comparable wireless 2-bar "reference-free" sensor electrode configuration under various conditions.

FIGS. 16A-C show the representative plots of a simultaneous comparison of sensor outputs between sensor embodiment 134 and a comparable two bar "reference free" sensor embodiment 234 attached in close proximity to one another on the skin 61 of a limb under conditions of: tapping the skin adjacent to sensor case (movement artifact plots 170; FIG. 16A); movement of the sensor in an electro-static field (electro-static artifact plots 180; FIG. 16B); and friction of a garment on the skin adjacent to the sensor (garment friction plots 190; FIG. 16C). In each of the FIGS. 16A-C, the sensor embodiment 134 is plotted on the upper trace and a comparable two bar "reference free" sensor embodiment 234 is plotted on the lower trace.

In FIG. 16A, the movement artifact plots 170 display a time region 171 containing multiple repetitions of tap induced artifact applied to the skin 61 in proximity to both sensor embodiments 134, 234. Over the time region 171, the sensor embodiment 134 indicates little or no artifact signal present in the output. During the same time region 171, the signal output from the two bar sensor embodiment 234 exhibits multiple large amplitude artifact responses, three of which are indicated 172.

In FIG. 16B, the electro-static artifact plots 180 display a time region 181 containing multiple repetitions of a simultaneous flexion and extension limb displacement of the sensor embodiments 134, 234 applied to the skin 61 with respect to a fixed electro-static field. Over the time region 181, the sensor embodiment 134 indicates little or no artifact signal present in the output. During the same time region 181, the signal output from the two bar sensor embodiment 234 exhibits multiple large amplitude artifact responses, three of which are indicated 182.

In FIG. 16C, the garment friction plots 190 display a time region 191 containing multiple repetitions of a simultaneous flexion and extension limb displacement of the sensor embodiments 134, 234 applied to the skin 61 of a limb covered by clothing fabric. Over the time region 191, the sensor embodiment 134 indicates little or no artifact signal present in the output. During the same time region 191, the signal output from the two bar sensor embodiment 234 exhibits multiple large amplitude artifact responses, three of which are indicated 192.

Other embodiments of the invention will be apparent to those skilled in the art from a consideration of the specification or practice of the invention disclosed herein. It is intended that the specification and examples be considered as exemplary only, with the true scope and spirit of the invention being indicated by the following claims.

What is claimed is:

1. A biomedical sensor for sensing phenomena of a muscle, comprising: a substrate; a plurality of conductive areas arranged to be spaced along a length of the substrate and configured as signal detection contacts each with a proximate, distinct respective associated signal reference contact, forming a plurality of signal detection/reference contact pairs spaced along the length, wherein each of the conductive areas is formed in the shape of at least one of: a disc attached to and coplanar with the substrate and a dome whose cross-sectional profile exhibits a concave curved shape attached to and projecting from the substrate and wherein each of the conductive areas is formed from a conductive plastic and wherein each one in the plurality of signal detection/reference contact pairs is aligned in a direction transversely to the length and in parallel with respect to each other so that each signal detection/reference contact pair produces movement induced artifacts in unison in response to relative movement between the plurality of signal detection/reference contact pairs and the muscle; and a differential sensing circuit that receives input from each of the signal detection/reference contact pairs and provides an output that is an arithmetic difference between the signals detected at detection contacts measured with respect to the reference contacts, the reference contacts being directly electrically coupled together and to a reference input of the differential sensing circuit, and the detection contacts being provided at separate inputs to the differential sensing circuit, wherein each signal detection/reference contact pair is configured to react in response to the relative movement, wherein at least one common electrical component caused by the relative movement is cancelled out by the differential sensing circuit, and wherein the at least one common electrical component caused by the relative movement includes the movement induced artifacts that are suppressed by the differential sensing circuit.

2. The biomedical sensor as in claim 1, wherein the substrate is rigid.

3. The biomedical sensor as in claim 1, further comprising: a framework coupled to the substrate, wherein the substrate is a body-directed electrically insulating bottom surface of the framework.

4. The biomedical sensor as in claim 1, wherein the plurality of signal detection/reference contact pairs are spaced apart so that the signal detection contact is aligned to be on the same side of each pair.

5. The biomedical sensor as in claim 1, wherein each of the conductive contact areas are formed of substantially identical material composition, size and shape.

6. The biomedical sensor as in claim 1, wherein the substrate is contoured in a concave shape to surround each of the conductive areas.

7. The biomedical sensor as in claim 1, further comprising: a framework coupled to the substrate, wherein the substrate is a body-directed electrically insulating bottom surface of the framework and wherein the framework includes a protective enclosure retaining wireless communication circuitry, associated control circuitry, power supply, and amplifier interconnected with a projecting portion of the contacts so that only the conductive areas are exposed.

8. The biomedical sensor as in claim 3, wherein framework includes an indicating marker aligned in parallel with a preferred orientation of the sensor with respect to a direction of signal propagation and delineating a location of signal input contacts.

9. The biomedical sensor as in claim 1, wherein the substrate is attached to skin with a double-sided adhesive membrane sheet with cut-out areas aligned with and matching a perimeter of each of the conductive areas.

10. A biomedical sensor for sensing phenomena of a muscle, comprising: a fixed framework; an electrically insulating substrate rigidly coupled to the fixed framework; a plurality of conductive areas symmetrically arranged to be spaced along a length of the electrically insulating substrate and configured as signal detection contacts, each being associated with a proximate, distinct signal reference contact to form a plurality of signal detection/reference contact pairs spaced along the length, wherein each of the conductive areas is formed in the shape of at least one of: a disc attached to and coplanar with the substrate and a dome whose cross-sectional profile exhibits a concave curved shape attached to and projecting from the substrate and wherein each one in the plurality of signal detection/reference contact pairs is aligned in a direction transversely to the length and in parallel with respect to each other so that each signal detection/reference contact pair produces movement induced artifacts in unison in response to relative movement between the plurality of signal detection/reference contact pairs and the muscle; and a differential sensing circuit coupled to the signal detection/reference contact pairs that provides an output that is an arithmetic difference between signals detected at the detection contacts measured with respect to the reference contacts, the reference contacts being directly electrically coupled together and to a reference input of the differential sensing circuit, and the detection contacts being provided at separate inputs to the differential sensing circuit, wherein each signal detection/reference contact pair is configured to react in response to the relative movement, wherein at least one common electrical component caused by the relative movement is cancelled out by the differential sensing circuit, and wherein the at least one common electrical component caused by the relative movement includes the movement induced artifacts that are suppressed by the differential sensing circuit.

11. The biomedical sensor as in claim 10, wherein the plurality of signal detection/reference contact pairs are spaced apart so that the signal detection contact is aligned to be on the same side of each pair.

12. The biomedical sensor as in claim 10, wherein the proximal arrangement is a side-by-side arrangement of the signal detection contact with the respective reference contact of each signal detection/reference contact pair, each signal detection contact being associated on a one-to-one basis with a different reference contact in each signal detection/reference contact pair.

13. The biomedical sensor as in claim 1, wherein the proximal arrangement is a side-by-side arrangement of the signal detection contact with the respective reference contact of each signal detection/reference contact pair, each signal detection contact being associated on a one-to-one basis with a different reference contact in each signal detection/reference contact pair.

* * * * *